United States Patent [19]

Hüber

[11] Patent Number: 4,925,152
[45] Date of Patent: May 15, 1990

[54] AIR TRAP FOR SHUTTING OFF FLEXIBLE PLASTIC TUBING

[76] Inventor: Karl-Alexander Hüber, Thüringer Strasse 28, D-7500 Karlsruhe - 41, Fed. Rep. of Germany

[21] Appl. No.: 299,883

[22] Filed: Jan. 19, 1989

[30] Foreign Application Priority Data

Jan. 21, 1988 [DE] Fed. Rep. of Germany ....... 3801577

[51] Int. Cl.$^5$ .............................................. F16K 7/07
[52] U.S. Cl. .................................... 251/5; 137/552; 604/67
[58] Field of Search ................ 251/4, 5, 7, 337; 137/552, 551; 604/34, 67, 250; 267/168, 182

[56] References Cited

U.S. PATENT DOCUMENTS

| | | | |
|---|---|---|---|
| 2,986,160 | 5/1961 | Acomb | 251/5 X |
| 3,823,724 | 7/1974 | Davis | 251/5 X |
| 3,882,899 | 5/1975 | Ginsberg et al. | 251/5 X |
| 4,797,655 | 1/1989 | Orndal | 604/67 X |

Primary Examiner—John C. Fox
Attorney, Agent, or Firm—Balogh, Osann, Kramer, Dvorak, Genova & Traub

[57] ABSTRACT

This invention relates to an air trap for shutting off flexible plastic tubing, particularly infusion tubing, for instance, during a transfusion of blood the air trap will reliably shut off the supply of blood when air bubbles are contained in the liquid entering the infusion tubing. This is ensured in that the air trap for shutting off flexible plastic tubing, particularly infusion tubing, comprises a flat head (mushroom-shaped head), which on one side bears on a ciaphragm, which defines a pressure chamber, and on the other side is provided with a guide stem, which is provided with means for squeezing a flexible plastic tubing in a receptacle and is operable to release the tubing in the receptacle under the action of a gas pressure in the pressure chamber and is spring-biased to cause said squeezing means to squeeze the flexible tubing in the receptacle when the pressure chamber is pressure-relieved.

5 Claims, 2 Drawing Sheets

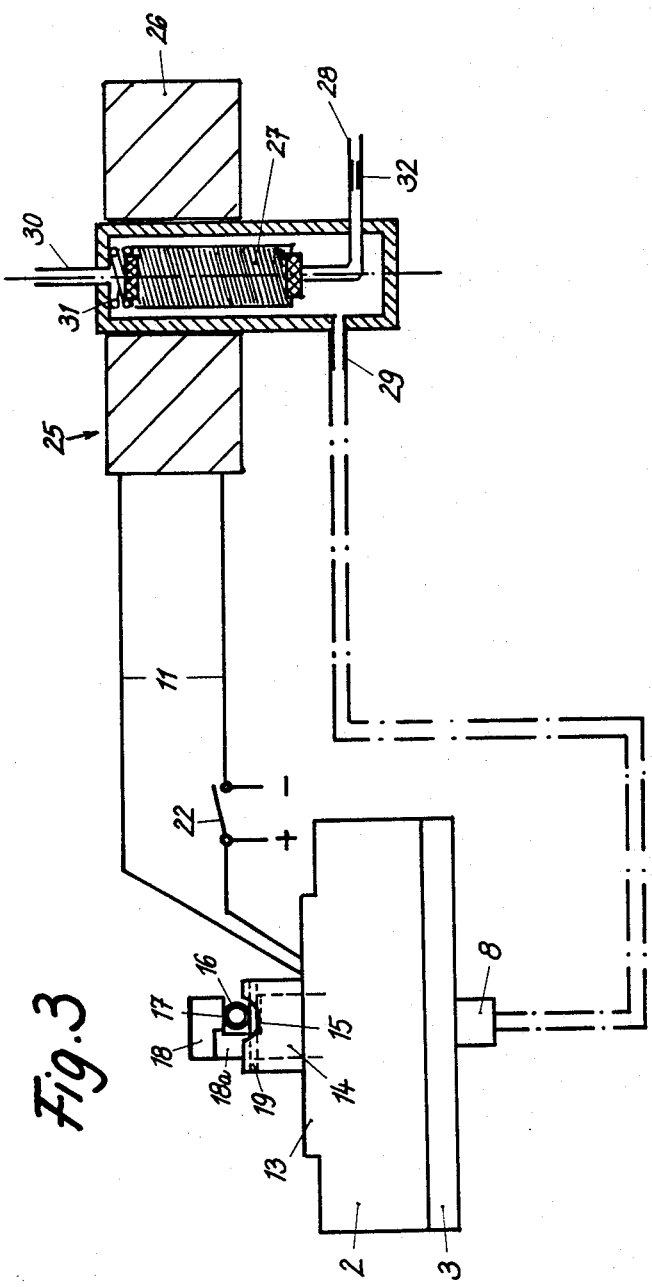

AIR TRAP FOR SHUTTING OFF FLEXIBLE PLASTIC TUBING

BACKGROUND OF THE INVENTION

1. Field of the Invention

This invention relates to an air trap for shutting off flexible plastic tubing, particularly infusion tubing.

2. Description of the Prior Art

For such purposes, air traps are known in which the flexible tubing is squeezed by pressure-applying rods, which are actuated by a piston against spring force. Such air traps are intended to ensure that in case of an interruption of the supply of liquid to be infused or other disturbances occurring during an infusion in which the infusion liquid is supplied under pressure to the circulatory system of the patient the infusion will be interrupted as soon as air bubbles occur in the tubing so that such air bubbles will not enter the circulatory system of the patient where they would will the patient. For instance, ozone-enriched patient blood may be returned to the circulatory system of the patient from the blood infusion bottle.

SUMMARY OF THE INVENTION

It is an object of the invention to provide an air trap for improving the safety—in addition to that afforded by the supervision by physicians and nursing staff who may drop out, e.g., by fainting— to ensure that the supply of blood will be interrupted when air bubbles occur in the injection tubing.

It is another object of the invention to provide such an air trap which can be used to advantage in other cases and environments, e.g., in flexible systems supplying liquid in chemical plants.

It is a further object of the invention to provide an air trap with which the objects mentioned hereinbefore are accomplished and which can be manufactured at low costs because it comprises fewer parts than known air traps of the same kind.

Said objects are accomplished in accordance with the invention by an air trap for shutting off flexible plastic tubing, particularly infusion tubing, which air trap comprises a flat head (mushroom-shaped head), which on one side bears on a diaphragm, which defines a pressure chamber, and on the other side is provided with a guide stem, which is provided with means for squeezing a flexible plastic tubing in a receptacle and is operable to release the tubing in the receptacle under the action of a gas pressure in the pressure chamber and is spring-biased to cause said squeezing means to squeeze the flexible tubing in the receptacle when the pressure chamber is pressure-relieved.

The pressure chamber is defined by two interconnected housing parts, particularly of plastic. The housing is formed on its inside surface with an annular recess, in which a diaphragm is fixed, which has the shape of a shallow bowl, and is engaged on one side by the flat head. The housing is provided on the other side of the diaphragm with an inlet port for connection to a compressed-gas line.

BRIEF DESCRIPTION OF THE DRAWING

FIG. 3 is a sectional view showing an overall arrangement.

DETAILED DESCRIPTION OF THE PREFERRED EMBODIMENT

Figure 2:
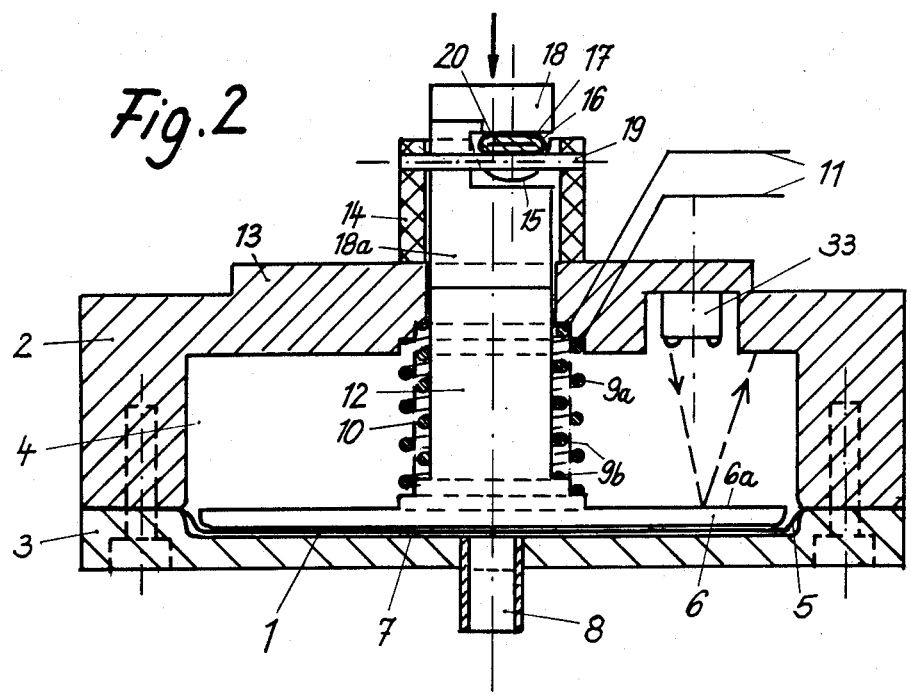
FIG. 2 is a sectional view showing the air trap of FIG. 1 in its closed position.

A preferred embodiment of the air trap in accordance with the invention will now be described more in detail with reference to the drawing.

Figure 1:
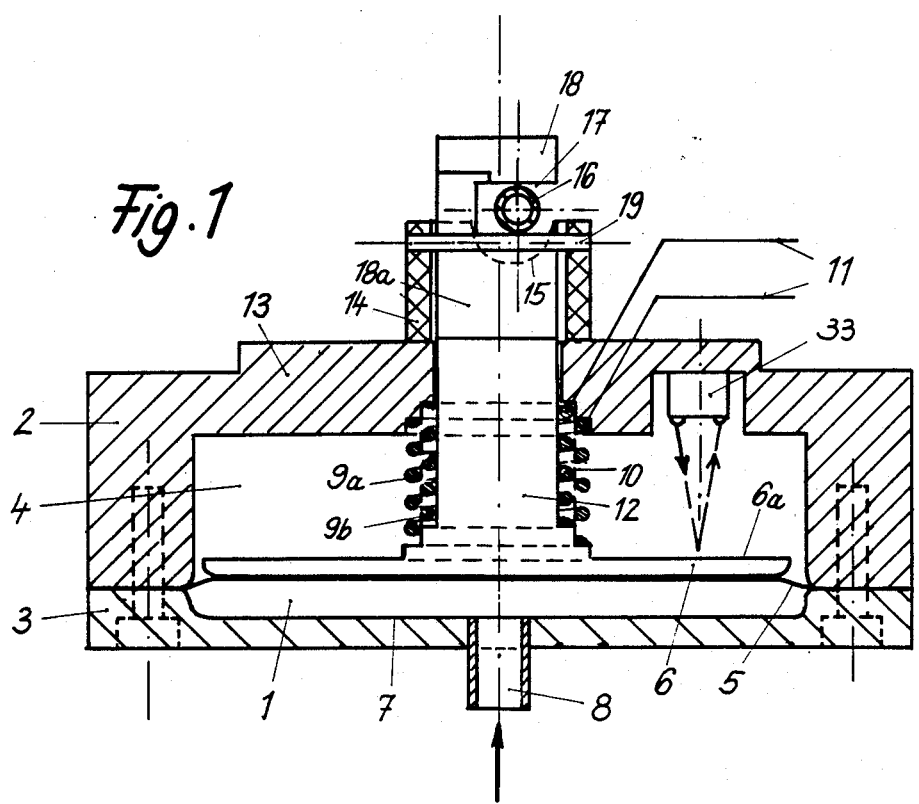
FIG. 1 is a sectional view showing the air trap when it is open.

In accordance with FIGS. 1 and 2 a pressure chamber 1 is defined by two interconnected housing parts 2, 3, which consist of plastic. The housing 2, 3 is formed on its inside surface with an annular recess 4, in which a diaphragm consisting of polytetrafluoroethylene and having the shape of a shallow bowl is secured. The diaphragm 5 is engaged at its top side by the flat head 6. On the underside of the diaphragm 5, the housing to a line for supplying compressed gas.

The flat head 6 is engaged at its top by two compression springs 9a, 9b, which are concentrically arranged one in the other and the peripheries of which are preferably electrically insulated from each other, e.g., by an insulating coil 10. The springs 9a, 9b are electrically connected in series and are flown through by an electric control current conducted in leads 11 of a control circuit. In case of a spring breakage, the control circuit will be interrupted so that the inlet port 8 will be shut off, as will be described hereinafter.

The flat head 6 is provided at its top with an upright guide stem 12, which carries at its top an upstanding tubular element 18a, which extends through the top wall 13 of the housing part 2 and through a receptacle or sleeve 14, which rises from the top wall 13 and is secured to or integral with the top walls 13. A crossbar 19 extends across the sleeve 14, which is formed in its top rim on opposite sides of the crossbar 19 with two concave recesses 15, which are aligned transversely to the crossbar 19 and together with the crossbar 19 define a passage 17 for receiving a flexible plastic tubing 16. The tubular element 18a is formed with two diametrically opposite vertical slots, through which the crossbar 19 extends so that the tubular element 18a is vertically movable by the guide stem 12 relative to the sleeve 14. The tubular element 18a is provided at its top end with a laterally protruding arm 18, which defines the passage 17 at its top when the pressure chamber 1 is pressure-relieved, the flat head 6 is operated by the springs 9a, 9b to lower the guide stem 12, the tubular element 18a and the arm 18 so that the latter squeezes the tubing 16 in the passage 17 against the crossbar 19.

Beyond each end of the passage 17, a light barrier is provided, which will be open when liquid such as blood is flowing through the tubing 16 and which upon an occurrence of air bubbles in the stream closes and causes control means, not shown, to open the switch 22 included in the circuit that includes the leads 11.

Conventional means for removably retaining the flexible tubing are provided at both ends of the passage 17 but are not shown here.

The air trap and specifically the passage 17 for the flexible plastic tubing 16 will be opened by the arm 18 against the action of the springs 9a, 9b in response to the application of pressure to the diaphragm 5 carrying the flat head 6 by a supply of compressed gas through the inlet port 8. This is controlled by a three-way valve 25, which comprises a magnetic core 27. In response to an energization of the solenoid coil 26, the magnetic core 27 is actuated to open the inlet port 28, which is connected, e.g., to a compressed oxygen bottle, and the transfer port 29 connected by a line to the inlet port 8 of the pressure chamber 1. The magnetic core 27 is biased by a spring 31 to close the ports 28 and 29 and to open the gas outlet port 30 to the atmosphere, as is shown in FIG. 3, in response to a deenergization of the solenoid coil 26. The action of the spring 31 on the magnetic core 27 is assisted by the action of the weight of the magnetic core. The inlet port 28 is constricted at 32 relative to the transfer port 29 and the gas outlet port 30 so that in case of the breakage of the spring 31 the gas flow will be throttled to such a degree that owing to the induced pneumatic drag the superatmospheric line pressure will not be sufficient to open the air trap and in case of a deenergization of the solenoid coil 26 the superatmospheric pressure of the inflowing gas from the port 28 can be relieved into the atmosphere through the gas outlet port 30. The force which is due to the weight of the magnetic core 27 must exceed the pneumatically exerted force by which the magnetic core 27 is urged against the body of the valve 25 around the outlet port 30.

The top wall 13 of the housing part 2 is formed in its inside surface with a recess, which contains a light barrier 33. The flat head 6 has a light-reflective surface at its top, i.e., on the side which is opposite to the diaphragm 5. In response to a pressurization of the pressure chamber 1 the diaphragm 5 is adapted to move said flat head 6 from an initial position to a releasing position in which the arm 18 entirely releases the tubing 16 in the passage 17. The light barrier 33 is adapted to emit light onto the light-reflective top surface of the flat head 6 and is adapted to receive reflected light from said light-reflective top surface when, and only when, said flat head 6 is in its releasing position. A time-measuring and comparator circuit is provided for controlling said three-way valve 25 for effecting a pressure relief of said pressure chamber when the interval of time from the beginning of the pressurization of said pressure chamber 1 by gas entering the valve 25 through the inlet port 28, which is constricted at 32, to the arrival of said flat head 6 in said releasing position as indicated by said light barrier 33 is shorter than a predetermined time. When that interval of time is shorter than the predetermined time, this will indicate that at least one of the springs 9a, 9b has been weakened by fatigue or has been broken. In that case the flexible tubing 16 will be squeezed in the passage 17 under the control of the above-mentioned time-measuring and comparator circuit, which will then cause the solenoid coil 26 to be deenergized so that the pressure chamber 1 is pressure-relieved. By that arrangement the reliability of the operation of the air trap may be improved in addition to the monitoring of the circuit by the springs 9a, 9b.

Because the flat head has a large surface, the present air trap may be operated with lower pressures. As a result, shorter compression springs may be used so that the air trap may have a smaller overall height than that shown on the drawing.

German Patent Specification 36 27 011 discloses an air trap which is similar to the one described hereinbefore and the disclosure thereof is incorporated herein by reference, particularly as regards the light barriers beyond each end of the passage 17 and the means for retaining the flexible tubing 16 in the passage 17.

I claim:

1. An air trap for shutting off flexible plastic tubing, comprising
   a body having a hollow interior and provided with an inlet port,
   a diaphragm disposed in said hollow interior and defining in said hollow interior a pressure chamber, which communicates with said inlet port,
   a guide stem, which is secured to said diaphragm on that side thereof that is opposite to said pressure chamber,
   a flat head coupled to said guide stem,
   valve means, which are connected to said inlet port and are operable to selectively pressurize and pressure-relieve said pressure chamber through said inlet port,
   a receptacle defining outside said body a passage for receiving a flexible tubing,
   squeezing means, which are operatively connected to and operable by said guide stem to release said tubing in said passage in response to gas pressure in said pressure chamber, and
   spring means biasing said flat head and guide stem to operate said squeezing means by said guide stem to squeeze said tubing in said passage in response to a pressure relief of said pressure chamber,
   wherein
   said spring means comprise two concentric compression springs, which are arranged one in the other and engage said flat head and urge it toward said pressure chamber,
   said valve means are electrically energizable to pressurize said pressure chamber and electrically deenergizable to pressure-relieve said pressure chamber,
   a control circuit for energizing and deenergizing said valve means is connected to said valve means, and
   said two compression springs are electrically connected in series in said control circuit.

2. An air trap as set forth in claim 1, which comprises insulating means for electrically insulating the peripheries of said two compression springs from each other.

3. An air trap for shutting off flexible plastic tubing, comprising
   a body having a hollow interior and provided with an inlet port,
   a diaphragm disposed in said hollow interior and defining in said hollow interior a pressure chamber, which communicates with said inlet port,
   a guide stem, which is secured to said diaphragm on that side thereof that is opposite to said pressure chamber, 'a flat head coupled to said guide stem,
   valve means, which are connected to said inlet port and are operable to selectively pressurize and pressure-relieve said pressure chamber through said inlet port,
   a receptacle defining outside said body a passage for receiving a flexible tubing,
   squeezing means, which are operatively connected to and operable by said guide stem to release said tubing in said passage in response to gas pressure in said pressure chamber, and
   spring means biasing said flat head and guide stem to operate said squeezing means by said guide stem to squeeze said tubing in said passage in response to a pressure relief of said pressure chamber,
   wherein
   a light barrier is disposed beyond each end of said passage and is arranged to be open when a colored liquid is flowing through said tubing in said passage and to be closed in response to an occurrence of air bubbles in said liquid, and control means are provided for operating said valve means to pressure-relieve said pressure chamber in response to the closing of at least one of said light barriers.

4. An air trap for shutting off flexible plastic tubing, comprising a body having a hollow interior and provided with an inlet port, a diaphragm disposed in said hollow interior and defining in said hollow interior a pressure chamber, which communicates with said inlet port, a guide stem, which is secured to said diaphragm on that side thereof that is opposite to said pressure chamber, a flat head coupled to said guide stem, valve means, which are connected to said inlet port and are operable to selectively pressurize and pressure-relieve said pressure chamber through said inlet port, a receptacle defining outside said body a passage for receiving a flexible tubing, squeezing means, which are operatively connected to and operable by said guide stem to release said tubing in said passage in response to gas pressure in said pressure chamber, and spring means biasing said flat head and guide stem to operate said squeezing means by said guide stem to squeeze said tubing in said passage in response to a pressure relief of said pressure chamber, wherein said flat head has a light-reflective surface on the side which is opposite to said diaphragm, a light barrier is provided in said housing on that side of said flat head which is opposite to said diaphragm, said diaphragm is adapted to move said flat head from an initial position to a releasing position in response to the pressurization of said pressure chamber, said light barrier is adapted to emit light onto said light-reflective surface and is adapted to receive light reflected from said light-reflective surface when, and only when, said flat head is in said releasing position, and time measuring and comparator means are provided for controlling said valve means for effecting a pressure relief of said pressure chamber when the time from the beginning of the pressurization of said pressure chamber to the arrival of said flat head in said releasing position as indicated by said light barrier is shorter than a predetermined time.

5. An air trap for shutting off flexible plastic tubing, comprising a body having a hollow interior and provided with an inlet port, a diaphragm disposed in said hollow interior and defining in said hollow interior a pressure chamber, which communicates with said inlet port, a guide stem, which is secured to said diaphragm on that side thereof that is opposite to said pressure chamber, a flat head coupled to said guide stem, valve means, which are connected to said inlet port and are operable to selectively pressurize and pressure-relieve said pressure chamber through said inlet port, a receptacle defining outside said body a passage for receiving a flexible tubing, squeezing means, which are operatively connected to and operable by said guide stem to release said tubing in said passage in response to gas pressure in said pressure chamber, and spring means biasing said flat head and guide stem to operate said squeezing means by said guide stem to squeeze said tubing in said passage in response to a pressure relief of said pressure chamber, wherein said valve means comprise a constricted inlet for compressed gas for pressurizing said pressure chamber.

* * * * *